US008865617B2

(12) United States Patent
Matsumoto

(10) Patent No.: US 8,865,617 B2
(45) Date of Patent: Oct. 21, 2014

(54) ORALLY ADMINISTERED ADSORBENT, METHOD OF PRODUCING THE SAME, AND DRUG PRODUCED BY USING THE SAME

(71) Applicant: Asahi Organic Chemicals Industry Co., Ltd., Nobeoka (JP)

(72) Inventor: Yasuhiro Matsumoto, Niwa-Gun (JP)

(73) Assignee: Asahi Organic Chemicals Industry Co., Ltd., Nobeoka-Shi (JP)

( * ) Notice: Subject to any disclaimer, the term of this patent is extended or adjusted under 35 U.S.C. 154(b) by 0 days.

(21) Appl. No.: 13/732,595

(22) Filed: Jan. 2, 2013

(65) Prior Publication Data

US 2013/0123095 A1   May 16, 2013

Related U.S. Application Data

(63) Continuation of application No. PCT/JP2011/064136, filed on Jun. 21, 2011.

(30) Foreign Application Priority Data

Aug. 2, 2010  (JP) .................................. 2010-173567
Feb. 28, 2011  (JP) .................................. 2011-042042

(51) Int. Cl.
   *B01J 20/00* (2006.01)
(52) U.S. Cl.
   USPC .......................................... 502/416; 502/418
(58) Field of Classification Search
   USPC .................................................. 502/416, 418
   See application file for complete search history.

(56) References Cited

U.S. PATENT DOCUMENTS

| 4,681,764 | A | 7/1987 | Endo et al. |
| 6,865,068 | B1 * | 3/2005 | Murakami et al. ............ 361/502 |
| 2004/0141963 | A1 | 7/2004 | Umekawa et al. |
| 2005/0079167 | A1 | 4/2005 | Sonobe et al. |
| 2005/0112114 | A1 | 5/2005 | Sonobe et al. |
| 2011/0142946 | A1 | 6/2011 | Tabata et al. |
| 2012/0225293 | A1 | 9/2012 | Matsumoto |

FOREIGN PATENT DOCUMENTS

| EP | 1 547 605 A1 | 6/2005 |
| JP | 56-073542 A1 | 6/1981 |
| JP | 11-228119 A1 | 8/1999 |
| JP | 2001-143973 A1 | 5/2001 |
| JP | 2004-244414 A1 | 9/2004 |
| JP | 3672200 B2 | 7/2005 |
| JP | 2006-015334 A1 | 1/2006 |
| JP | 2006-111604 A1 | 4/2006 |
| JP | 3835698 B2 | 10/2006 |
| JP | 2010-106007 A1 | 5/2010 |
| JP | 2011-157464 A1 | 8/2011 |
| WO | 2010/086985 A1 | 8/2010 |

OTHER PUBLICATIONS

"Inorganic Acids". Sigma Aldrich. 2013. <http://www.sigmaaldrich.com/chemistry/chemistry-products.html?TablePage=16281080> Accessed Oct. 15, 2013.*
Generic Drug Quality Information Review Conference Material 4-1-2 (report on the quality of spherical carbon adsorbent drug), Dec. 25, 2009, pp. 1-7.
International Search Report dated Jul. 26, 2011.
U.S. Appl. No. 13/961,349, filed Aug. 7, 2013, Matsumoto et al.

* cited by examiner

*Primary Examiner* — Richard M Rump
(74) *Attorney, Agent, or Firm* — Burr & Brown, PLLC

(57) ABSTRACT

An orally administered adsorbent which has a high ability of adsorbing indoxylsulfuric acid, indoleacetic acid, and indole, a method permitting easy and advantageous production of the same, and a drug using the same. The orally administered adsorbent is obtained from spherical particles of activated carbon by carbonizing and activating spherical particles of a furfuryl alcohol resin obtained by resinifying furfuryl alcohol through a self-condensation reaction and curing the resinified furfuryl alcohol.

8 Claims, No Drawings

US 8,865,617 B2

ORALLY ADMINISTERED ADSORBENT, METHOD OF PRODUCING THE SAME, AND DRUG PRODUCED BY USING THE SAME

This application is a continuation of the International Application No. PCT/JP2011/064136, filed Jun. 21, 2011, which claims the benefit under 35 U.S.C. §119(a)-(d) of Japanese Application No. 2010-173567, filed Aug. 2, 2010, and Japanese Application No. 2011-042042, filed Feb. 28, 2011, the entireties of which are incorporated herein by reference.

BACKGROUND OF THE INVENTION

1. Field of the Invention

The present invention relates to an orally administered adsorbent, a method of producing the same, and a drug produced by using the same, and more particularly to an orally administered adsorbent comprising spherical particles of activated carbon obtained by using spherical particles of furfuryl alcohol resin, a method of advantageously producing the same, and a drug produced by using the same.

2. Discussion of Related Art

Conventionally, an orally administered adsorbent is orally administered to a patient of a renal disease, for example, in order to adsorb uremic toxins and prevent a progress of renal failure. The orally administered adsorbent has been produced by using pitch materials. However, there is a problem that the conventional orally administered adsorbent derived from the pitch materials adsorbs digestive enzymes together with uremic toxins. Therefore, there have been recently developed techniques for producing orally administered adsorbents which selectively adsorb uremic toxins having a relatively small molecular size, such as β-aminoisobutyric acid, such that the adsorbents are produced by using a thermosetting resin such as a phenolic resin and an ion-exchange resin (Patent Documents 1-5). Such adsorbents are commercially available.

However, the conventional orally administered adsorbents are still insufficient in their ability of adsorption of major constituents of uremic toxins, and their ability of adsorption of indoxylsulfuric acid (most widely used uremia-related marker), in particular, is not clarified. "4th Generic Drug Quality Information Review Conference Material 4-1-2" (Non-Patent Document 1) discloses that a commercially available orally administered adsorbent obtained by using a thermosetting resin (phenolic resin) has an insufficient ability of adsorption of indoxylsulfuric acid, and indicates a problem that the ability of adsorption of indoxylsulfuric acid has to be improved.

Further, the orally administered adsorbents proposed in the above-indicated Patent Documents 1-5 are produced by using a petrochemical resource as their starting materials, and therefore cannot sufficiently meet a recent requirement for reducing carbon dioxide emissions.

PRIOR-ART DOCUMENTS

Patent Documents

Patent Document 1: JP-A-56-73542
Patent Document 2: JP-A-2004-244414
Patent Document 3: JP-A-2006-15334
Patent Document 4: Japanese Patent No. 3672200
Patent Document 5: Japanese Patent No. 3835698

Non-Patent Document

Non-Patent Document 1: Generic Drug Quality Information Review Conference Material 4-1-2 (report on quality of spherical carbon adsorbent drug)

SUMMARY OF INVENTION

The present invention was made in view of the above-described potential problems of the conventional orally administered adsorbents. It is therefore an object of the invention to provide an orally administered adsorbent having a high ability of adsorption of indoxylsulfuric acid, indoleacetic acid and indole, which are uremic toxins that are compounds whose chemical formulas include an indole skeleton. It is another object of the invention to provide a method of easily and advantageously producing the adsorbent. It is a further object of the invention to provide a spherical orally administered adsorbent which can meet the requirement for reducing carbon dioxide emissions by permitting the use of a biomass-derived material. It is a still further object of the invention to provide a method of producing the adsorbent. It is a yet further object of the invention to provide an orally administered drug produced by using the adsorbent.

Various studies made by the present inventor in an effort to achieve the above-described objects revealed that a high ability of adsorption of indoxylsulfuric acid, indoleacetic acid and indole can be achieved by spherical particles of activated carbon formed of spherical particles of a furfuryl alcohol resin obtained as a thermosetting resin by using a furfuryl alcohol material made from cores of corns, for example, and by resinifying the furfuryl alcohol material through a self-condensation reaction, and by curing the resinified furfuryl alcohol material. The inventor conducted a further study based on the above-described finding and made the present invention.

Namely, the present invention provides an orally administered adsorbent, characterized by comprising spherical particles of activated carbon formed by carbonizing and activating spherical particles of a furfuryl alcohol resin obtained by resinifying furfuryl alcohol through a self-condensation reaction and by curing the resinified furfuryl alcohol.

According to one preferred form of the orally administered adsorbent according to the present invention, the adsorbent has an average particle diameter of 150-1000 μm and a specific surface area of 1000-1800 $m^2/g$ measured by the BET method.

The present invention further provides a method of easily and advantageously producing an orally administered adsorbent, characterized by comprising the steps of: (a) providing spherical particles of a furfuryl alcohol resin obtained by a self-condensation reaction of furfuryl alcohol and curing of the self-condensation reaction product; (b) obtaining spherical particles of carbon by carbonizing the spherical particles of the furfuryl alcohol resin at a temperature of 400-900° C.; and (c) forming spherical particles of activated carbon by activating the obtained spherical particles of carbon at a temperature of 700-1000° C.

According to a preferred form of the method of the present invention, the spherical particles of the furfuryl alcohol resin provided in the above-indicated step (a) are produced by a reaction of the furfuryl alcohol in the presence of an acid catalyst and a protective colloid.

According to further preferred forms of the method of producing the orally administered adsorbent according to the present invention, the protective colloid is a water-soluble high-molecular compound. Specifically, gum arabic is advantageously used as the protective colloid. The acid catalyst has a pKa of less than 1.5. Specifically, alkylbenzene sulfonic acid is advantageously used as the acid catalyst. Preferably, the reaction of the furfuryl alcohol is conducted in the presence of water as a reaction medium at a temperature of not lower than 50° C. According to a yet further preferred form of the method of the invention, the obtained spherical particles of activated carbon are subjected to oxidizing and/or reducing treatment(s) so as to modify a surface condition of the spherical particles of the activated carbon.

An orally administered drug comprising the orally administered adsorbent according to the present invention as an effective component thereof is used to adsorb toxins in digestive organs and particularly advantageously used as a drug for curing and prevention of a renal disease. The renal disease include chronic kidney disease (chronic renal failure), acute kidney injury (acute renal failure), chronic nephritic syndrome, acute nephritic syndrome, rapidly progressive nephritic syndrome, nephrotic syndrome, recurrent/persistent hematuria, chronic pyelonephritis, acute pyelonephritis, tubulointerstitial nephritis, diabetic nephropathy, nephrosclerosis, renovascular hypertension, and secondary glomerulonephritis.

According to the present invention, there is advantageously provided the orally administered adsorbent which has a significantly improved ability of adsorption of indoxylsulfuric acid, indoleacetic acid and indole, and which is composed of the spherical particles of activated carbon obtained from the spherical particles of the furfuryl alcohol resin. The orally administered adsorbent having the above-indicated excellent properties can be easily and advantageously produced according to the present invention.

The orally administered adsorbent according to the present invention is produced by using furfuryl alcohol, which is a biomass-derived material, making it possible to sufficiently meet the recent requirement for reducing carbon dioxide emissions. In this respect, the present invention can provide an orally administered adsorbent contributable to environmental protection, a method of producing the same and an orally administered drug produced by using the same.

DETAILED DESCRIPTION OF THE INVENTION

An orally administered adsorbent according to the present invention comprises spherical particles of activated carbon formed by carbonizing and activating spherical particles of a furfuryl alcohol resin obtained by resinifying furfuryl alcohol through a self-condensation reaction and curing the resinified furfuryl alcohol. The orally administered adsorbent advantageously has an average particle diameter of 150-1000 μm and a specific surface area (BET specific surface area) of 1000-1800 $m^2/g$ measured by the BET method. The ability of adsorption of toxins can be further improved by preparing the adsorbent so as to have the above-indicated average particle diameter and BET specific surface area.

In the production of the orally administered adsorbent according to the present invention, in order to obtain the spherical particles of the furfuryl alcohol resin to be used as the starting material, furfuryl alcohol is resinified through a self-condensation reaction in the presence of water as a reaction medium, an acid catalyst and a protective colloid. The resinification is followed by heating of the resinified furfuryl alcohol for curing. Then, a liquid reaction product containing the produced resin particles is filtered and purified to obtain fine spherical particles having an average particle diameter of about 150-1000 μm. As the furfuryl alcohol to be used for producing the resin particles, biomass-derived ones obtained from cores of corns, for example, are preferably used for contribution to environmental protection by reducing carbon dioxide emissions.

The protective colloid, which is present in the reaction system of such furfuryl alcohol, is added to make the furfuryl alcohol resin in a fine spherical particulate form. Any conventionally known protective colloid may be used. Examples of the protective colloid that are suitably used in the present invention include, but are not limited to, water-soluble high-molecular compounds, such as gum arabic, gum ghatti, hydroxyl alkyl guar gum, partially hydrolyzed polyvinyl alcohol, hydroxyethyl cellulose, hydroxypropyl cellulose, and carboxymethyl cellulose. Especially, gum arabic is preferably used in the present invention.

Any one of, or any combination of the protective colloids may be used. Further, a surfactant may be used together with the protective colloid. Although an amount of the protective colloid is suitably determined depending on the kind of the protective colloid to be used, the protective colloid is generally added at a ratio of about 0.1-10% by mass, preferably about 0.5-5% by mass, and more preferably about 1-3% by mass, with respect to the furfuryl alcohol.

In the present invention, together with the above-described protective colloid, a suitable acid catalyst, preferably an acid catalyst having a pKa of less than 1.5 is used as a catalyst for a self-condensation reaction (resinification) of the furfuryl alcohol and curing of the resinified furfuryl alcohol. The acid catalyst allows the produced furfuryl alcohol resin to be effectively microparticulated, thereby advantageously producing the fine spherical particles having an average diameter of about 150-1000 μm. The use of the acid catalyst having a pKa of more than the upper limit may cause insufficient self-condensation (resinification) of the furfuryl alcohol and insufficient curing of the resinified furfuryl alcohol, and ineffective microparticulation of the resin particles.

Examples of suitable acid catalysts for use in the invention include hydrochloric acid, sulfuric acid, nitric acid, oxalic acid, trifluoroacetic acid, methanesulfonic acid, benzenesulfonic acid, para toluene sulfonic acid, phenolsulfonic acid, decylbenzene sulfonic acid, dodecylbenzene sulfonic acid, tetradecyl benzene sulfonic acid, hexadecyl benzene sulfonic acid, and octadecyl benzene sulfonic acid. Any one of, or any combination of the above-described acid catalysts may be used. Advantageously, alkylbenzene sulfonic acid, especially alkylbenzene sulfonic acid having an alkyl group of 10 or more carbon atoms is favorably used. In view of economy, availability and catalytic function, it is especially recommended to use the dodecylbenzene sulfonic acid.

The amount of the acid catalyst is suitably determined depending on the reaction condition of the furfuryl alcohol, and further depending on the kind of the protective colloid. Generally, the acid catalyst is used at a ratio of about 0.1-10% by mass, preferably about 0.5-7% by mass, and more preferably about 1-5% by mass, with respect to the furfuryl alcohol. When the acid catalyst is used at a ratio of less than the lower limit, the objects of the present invention may not be sufficiently achieved. On the other hand, when the acid catalyst is used at a ratio of more than the upper limit, a large amount of bubbles is generated during the reaction, making it difficult to uniformly stir the reaction liquid, so that fine particles cannot be produced.

Further, the amount of water as the reaction medium for use in the self-condensation reaction (resinification) of the furfuryl alcohol and for use in the progress of the curing reaction is determined depending on the reaction condition and the like. Generally, the amount of water is about 0.5-25 times by mass, preferably about 1-20 times by mass, and more preferably about 5-15 times by mass, with respect to the amount of the furfuryl alcohol. The amount of water which is less than 0.5 times by mass with respect to the furfuryl alcohol may cause agglomeration of the reaction product, for example. The amount of water which is larger than 25 times by mass with respect to the furfuryl alcohol may require an excessively long reaction time and reduce the economy of production.

Generally, the self-condensation reaction (resinification) of the furfuryl alcohol and the curing (cross-linking) of the resinified furfuryl alcohol in accordance with the present invention is, in view of the reaction efficiency, conducted at a temperature not lower than 50° C., preferably at a temperature not lower than 70° C., and more preferably at a temperature not lower than 80° C., in order to microparticulate the resin to be produced. The self-condensation reaction (resinification) and the curing (cross-linking) reaction can be conducted in separate steps. In the present invention, it is advantageous that the curing reaction is successively conducted following the self-condensation reaction. Further, the two reaction steps may be conducted at the same temperature, or the curing (cross-linking) reaction may be conducted at a higher temperature than the self-condensation reaction (resinification). Further, the reaction time is suitably determined in view of conditions such as the reaction temperature, the amount of water in the reaction system, and the conditions of the condensation and curing of the product. Generally, a total of about 1-50 hours is required for the two reactions.

The spherical particles of the furfuryl alcohol resin to be used in the present invention are obtained as spherical resin particles having an average particle diameter of about 150-1000 μm, by filtering and purifying the liquid reaction product containing the resin particles produced through the reaction of the furfuryl alcohol as described above.

Then, the thus obtained spherical particles of the furfuryl alcohol resin are carbonized by a conventional method using a device such as a rotary kiln in a non-oxidizing atmosphere of nitrogen, helium or argon, for example. Advantageously, the spherical particles of the furfuryl alcohol resin are fired at a temperature of 400-900° C. to be carbonized. When the carbonization temperature is too low, it is difficult to effectively carbonize the resin particles. When the carbonization temperature is too high, carbonization of the spherical particles excessively progresses, giving rise to problems such as deterioration of the spherical shape and deterioration of properties of the carbonized particles.

The desired spherical particles of activated carbon are formed by subjecting the thus obtained spherical particles of carbon to a suitable activating treatment, and are used as the orally administered adsorbent according to the present invention. The activating treatment of the spherical particles of carbon can be conducted according to a conventional method. For example, the desired particles of activated carbon can be advantageously formed by conducting the activating treatment at a temperature of 700-1000° C. in a stream of steam or $CO_2$ gas, for example, which is reactive with carbon. The activating step may be successively conducted following the above-described carbonizing step or may be independently conducted as a separate step.

After the activating step, one or a combination of an oxidizing treatment and a reducing treatment may be conducted with respect to the obtained spherical particles of activated carbon in order to control the functional group and the selective adsorption of their surfaces. Generally, the oxidizing treatment is conducted by oxidizing the particles of activated carbon in an oxidizing atmosphere at a temperature of 400-550° C. The reducing treatment is conducted by deoxidizing the particles of activated carbon in an atmosphere of an inert gas such as nitrogen gas at a temperature of 700-900° C. The spherical particles of activated carbon whose surface condition is modified by the oxidizing and/or reducing treatment(s) have acidic and basic sites added on their surfaces in a well-balanced manner, and exhibit an advantageously increased ability of adsorption of toxins in the intestine, when the spherical particles are orally administered.

The orally administered adsorbent comprising the spherical particles of activated carbon is orally administered to a patient of a renal disease, for example, in a conventional form such as powders, granules, tablets, sugar-coated tablets, capsules, suspensions, sticks, divided packages, emulsions and jellies, according to the object of administration. In the case of capsules, the usual gelatin capsules, or if necessary, enteric capsules may be used. In the case of tablets, the tablets must be broken within the body, into the original fine particles. The adsorbent may be used as a mixture with other drug or an electrolyte-controlling agent, for example.

The thus obtained orally administered adsorbent according to the present invention comprises spherical particles of activated carbon obtained by using spherical particles of the furfuryl alcohol resin as the starting material, and exhibits a high ability of adsorption of toxins such as indoleacetic acid and indole, as well as indoxylsulfuric acid, which is an essential marker of uremia. The reason for this has not been revealed yet, but the present inventor presumes that the firing of the spherical particles of the furfuryl alcohol resin generates a carbon structure different from that generated during production of a conventional adsorbent, since the furfuryl alcohol resin, which is used as the starting material in the present invention, is a resin having a five-membered ring comprising atoms of carbon, hydrogen and oxygen, and is different from the phenolic resin, for example, which is conventionally used as a starting material and mainly comprising a six-membered ring (benzene ring) comprising atoms of carbon, hydrogen and oxygen. It is considered that the different carbon structure permits the orally administered adsorbent according to the present invention to obtain functions and effects superior to the conventional orally administered adsorbent.

The orally administered adsorbent according to the present invention is used for medicine, and particularly preferably used as an orally administered drug for curing and prevention of a renal disease. When a person suffers from a renal disease, toxins inside the body, such as indoxylsulfuric acid, indoleacetic acid and indole, cannot be sufficiently excreted from the body together with urine due to a loss of renal function, so that uremia is developed. By administering the orally administered drug comprising the orally administered adsorbent according to the present invention as an effective component, it is possible to adsorb toxins in the intestine and excrete the toxins together with feces, thereby effectively suppressing absorption of toxins inside the body. Thus, the orally administered adsorbent according to the present invention improves symptoms of uremia and can be advantageously used as the orally administered drug for curing and prevention of a renal disease. The orally administered adsorbent according to the present invention can be used for diseases other than the renal disease as long as the symptom can be suppressed or resolved by adsorbing toxins in digestive organs.

The above-described renal disease includes chronic kidney disease (chronic renal failure), acute kidney injury (acute renal failure), chronic nephritic syndrome, acute nephritic syndrome, rapidly progressive nephritic syndrome, nephrotic syndrome, recurrent/persistent hematuria, chronic pyelonephritis, acute pyelonephritis, tubulointerstitial nephritis, diabetic nephropathy, nephrosclerosis, renovascular hypertension, or secondary glomerulonephritis. The orally administered adsorbent according to the present invention may also be used for a disease which is caused by or intercurrent with a renal disease. The orally administered adsorbent according to the present invention is preferably used as the orally administered drug for curing and prevention of renal failure, in particular, which presents symptoms of uremia.

Renal failure is a condition in which kidney function (renal function) decreases for various causes, and waste products and aqueous components, which are normally excreted as urine, stay in the blood. As the renal failure progresses, various symptoms such as uremia are presented. The renal failure is classified into acute kidney injury, which presents a rapidly progressive loss of the renal function, and chronic kidney disease, which presents a gradual loss of the renal function over a long period of time.

The chronic kidney disease causes a gradual loss of functions of the glomeruli and the renal tubule in the kidney, making it impossible to maintain the internal environment of the body by the renal function. Initial symptoms of the chronic kidney disease include hypertension and hyperglycemia. It is considered that when glomerular hypertension continues due to a long-term hypertension, arteriolar nephrosclerosis, namely, glomerulosclerosis is developed. The glomerulosclerosis presents proteinuria, which adds a load to the renal tubule and causes gradual hardening of the kidney tissue in combination with fibrosis due to inflammation, leading to nephrosclerosis. As the symptom progresses, the blood flow level in the kidney declines, giving rise to a difficulty in filtration of waste products and aqueous components, and causing a vicious circle of aggravation of the symptom of hypertension. Further, hypertension may cause arteriosclerosis, fibromuscular dysplasia, and aortitis syndrome, which narrow the renal artery and lead to renovascular hypertension. Hyperglycemia develops diabetic nephropathy resulting from kidney malfunction when blood sugar control is out of order for a long period of time. Diabetic nephropathy tends to develop when a patient has suffered from diabetes for a long period of time, gradually presenting proteinuria and resulting in nephrotic syndrome, which causes edema, and deterioration of the renal function. When diabetes develops, active oxygen inhibits production of insulin and causes mutation of mitochondria, increasing the glucose level in the blood. When the increased glucose reacts with protein, for example, active oxygen attacks the tissue or organ where the reaction occurred, developing complications such as renal failure and neuropathy. An increase of active oxygen leads to an increase of oxidative stress, which causes renal failure, a circulatory disease, cerebral apoplexy, and arteriosclerosis, for example.

When the symptom of the chronic kidney disease further progresses, there are caused renal anemia, metabolic acidosis, hyperphosphatemia, hypocalcemia, and hyperkalemia, for example. Renal anemia is caused by reduction of the blood creating function due to reduction of the renal function, which inhibits secretion of erythropoietin that functions as a hormone for promoting production and assisting growth of red blood cells. Metabolic acidosis is a condition in which the acid-base balance inside the body is on the side of acidic state due to a loss of base, an increase of inorganic acid other than bicarbonic acid, or an increase of (involatile) organic acid. Hyperphosphatemia is a condition in which phosphorus stays in the blood due to reduction of elimination of phosphorus from the kidneys. When hyperphosphatemia is developed, phosphorus does not dissolve in the blood but combines with calcium and is calcified at joints, for example. The calcification of phosphorus causes an ischemic heart disease, giving rise to a risk of developing myocardial infarction and angina pectoris. When a high concentration of phosphorus in the blood continues, secretion of parathyroid hormone which directly acts on bones is promoted, causing secondary hyperparathyroidism and presenting complications such as bony distortion, fracture and bone ache. Hypocalcemia is a condition in which the concentration of calcium ion in the blood plasma is reduced due to reduction of reabsorption of calcium ion from the bones and kidneys, reduction of absorption of calcium ion from the digestive tracts, and chelation of serum calcium, for example. When hypocalcemia continues, secondary hyperparathyroidism develops due to hyperplasia of chief cells of the parathyroid gland. Hyperkalemia is one of electrolyte metabolism disorders, which causes an increase of concentration of potassium in the blood.

When a symptom of the chronic kidney disease reaches a terminal stage, there are caused various kinds of uremic symptoms in the digestive system, nervous system and circulatory system. In the digestive system, there are caused bad breath, vomiting, stomach inflammation, gastrointestinal bleeding, gastric ulcer, pancreatitis, for example. In addition, the liver, which is correlated to the kidneys, is significantly affected. A liver disease may be caused by toxins which cannot be excreted from the kidneys due to reduction of the renal function and reach the liver through the blood vessels. Alternatively, the liver disease may be caused under an influence of toxins inside the digestive organs independently of a renal disease. Therefore, the orally administered adsorbent according to the present invention is also effective for curing and prevention of the liver disease. In the nervous system, there are caused disorders in the central nervous system, psychiatric system and peripheral nervous system. In the circulatory system, there are caused symptoms such as a disorder of the blood pressure, pericarditis, myocarditis, anemia, and uremic lung. Further, there are caused: a disorder of the endocrine glands; metabolic disorder; eye symptoms such as retinopathy and keratopathy; symptoms of anemia; and skin symptoms such as pigmentation, pruritus cutanea and subcutaneous bleeding.

Nephritis is inflammation of the kidney and is classified depending on the main part of the kidney where the inflammation occurs. The kidney consists mainly of the glomerulus tissue for filtrating the urine, the renal tubule and the interstitium around the glomerulus tissue, and the renal pelvis which connects the kidney and the ureter. Nephritis is classified into glomerulonephritis, tubuiointerstitial nephritis and pyelonephritis. The renal tubule is a fine tube through which the body fluid and waste products removed from the blood in the glomeruli are carried to tubes for excreting the urine to the renal pelvis.

Glomerulonephritis is classified into primary and secondary types of glomerulonephritis. The primary type of glomerulonephritis includes acute nephritic syndrome, rapidly progressive nephritic syndrome, chronic nephritic syndrome, nephrotic syndrome, and recurrent/persistent hematuria. The acute nephritic syndrome presents rapidly developing renal failure such as hematuria and proteinuria, and edema and hypertension accompanying the renal failure. The chronic nephritic syndrome is a syndrome which gradually develops and progresses, or an acute nephritic syndrome which has become chronic. The chronic nephritic syndrome includes minimal-change disease, focal (segmental) glomerulonephritis, focal glomerulosclerosis, mesangium proliferative glomerulonephritis, membranous nephropathy, membranoproliferative glomerulonephritis, dense deposit glomerulonephritis, sclerosing glomerulonephritis, and IgA nephropathy. The rapidly progressive nephritic syndrome presents a rapid progress of renal dysfunction and large-scale glomerular crescent formation. The rapidly progressive nephritic syndrome progresses into terminal-stage renal failure within several weeks to several months if left untreated. Most of recurrent/persistent hematuria is inactive IgA nephropathy or an acute nephritic syndrome which has become chronic. The nephrotic syndrome is a collective term for renal disease group which leads to hypoproteinemia due to severe proteinuria. Nephrotic syndrome includes minimal-change disease, focal segmental glomerulosclerosis, membranous glomerulonephritis, congenital/infantile nephrotic syndrome, membranoproliferative glomerulonephritis, and mesangium proliferative glomerulonephritis, and presents symptoms of uremia as reduction of the renal function progresses. The secondary type of glomerulonephritis includes lupus nephritis, purpura nephritis, and nephritis accompanying a liver disease, and exhibits lesion of glomeruli accompanying various diseases. The nephritis accompanying a liver disease includes IgA nephropathy and membranous nephropathy, which accompany viral hepatitis and cirrhosis, for example. Hematuria and proteinuria, which are symptoms of glomerulonephritis, cause an asymptomatic hematuria/proteinuria syndrome which may lead to a chronic kidney disease when the symptom progresses.

Tubulointerstitial nephritis is inflammation of the renal tubule and the interstitium. When the renal tubule and the tubular interstitial tissue are damaged by inflammation, the kidneys cannot condense the urine, making it difficult to excrete metabolic waste products and to maintain a balance of excretion of electrolytes such as sodium and potassium. Tubulointerstitial nephritis is classified into acute tubulointerstitial nephritis and chronic tubulointerstitial nephritis. Acute tubulointerstitial nephritis is caused mainly by a side effect of a drug and sometimes caused as an infectious disease of acute pyelonephritis or a complication of a collagen disease. Chronic tubulointerstitial nephritis is caused mainly as a chronic infectious disease of chronic pyelonephritis. Both of the acute and chronic tubulointerstitial nephritis present symptoms of renal failure. Sometimes, nephritis causes inflammation of the vessels in the kidneys which is called angiitis.

Pyelonephritis is inflammation inside the kidneys caused by a bacterial infection of the renal pelvis which connects the kidneys to the ureter, and classified into chronic and acute types of pyelonephritis. The chronic type of pyelonephritis often has an underlying disease such as urolithiasis, prostatauxe, and urinary tract malformation. The acute type of pyelonephritis is often caused by colibacillus ascending from the urinary bladder to the renal pelvis through the ureter. A renal failure tends to be caused when pyelonephritis recurs many times or has become chronic.

In the present invention, in order to deal with the above-described renal diseases and diseases caused by the renal diseases, administration of the orally administered drug comprising the orally administered adsorbent according to the present invention as an effective component makes it possible to adsorb toxic substances such as toxins in the intestine, and excrete them with feces, thereby advantageously eliminating the toxins which have not been eliminated with urine due to reduction of the renal function and remain inside the body. Thus, the orally administered drug according to the present invention can be used for curing a renal disease by suppressing aggravation of the symptoms caused by the toxic substances. The orally administered drug can also be used as a depressant or preventive drug for suppressing the above-described symptoms before developing from renal diseases.

Further, the orally administered adsorbent according to the present invention can be used for curing and prevention of an intercurrent disease of a renal disease. The intercurrent disease of a renal disease includes a renal bone abnormal nutrition symptom. Uremia causes hyperphosphatemia accompanying reduction of the renal function, reduction of absorption of calcium in the intestine, and reduction of reactivity of the bone to parathyroid hormone, and develops hypocalcemia. Hypocalcemia and reduction of the function of restricting parathyroid hormone cause secondary hyperparathyroidism, which, in combination with metabolic acidosis, develops the renal bone abnormal nutrition symptom. The renal bone abnormal nutrition symptom is a term collectively representing all metabolic bone changes which are intercurrent with chronic kidney diseases, and includes osteomalacia, osteoporosis, osteosclerosis, and osteitis fibrosis, for example. By administering the orally administered adsorbent according to the present invention, it is possible to recover the renal function so as to restrict reduction of absorption of calcium in the intestine, thereby preventing reduction of the bone mass. Thus, the orally administered adsorbent can be used as a drug for preventing and improving the renal bone abnormal nutrition symptom.

Further, hyperuricemia is sometimes developed by reduction of excretion of uric acid due to a renal disease. When hyperuricemia progresses, uric acid does not dissolve inside the body and crystallizes at joints, for example, giving rise to a disorder such as gout, and causing an ischemic heart disease such as myocardial infarction. Therefore, the orally administered adsorbent according to the present invention can be used for preventing and improving hyperuricemia and gout, for example, when the adsorbent is administered as an orally administered drug so as to improve the renal disease.

The orally administered drug comprising the orally administered adsorbent according to the present invention as an effective component can be administered to animals such as dogs and cats as well as human being. A dosage of the orally administered drug depends on whether it is administered to the human being or other animals, and on their age, height, weight, and condition of disease. Therefore, in some cases, a dosage outside the dosage indicated below may be appropriate, but in general, the oral dosage of the adsorbent in the case of the human being is usually 1-20 g per day, and the daily dosage may be divided into three or four portions. The dosage may appropriately vary with the condition of disease.

EXAMPLES

To further clarify the present invention, some examples of the invention will be described. However, it is to be understood that the invention is not limited to the details of the illustrated examples and the foregoing description, but may be embodied with various changes, modifications, and improvements, which may occur to those skilled in the art without departing from the spirit of the invention. In the following examples, "parts" and "%" mean "parts by mass" and "% by mass", unless otherwise specified.

A BET specific surface area, volume mean particle diameter, and an ability of adsorption of indole, indoleacetic acid and indoxylsulfuric acid of the orally administered adsorbents (specimens) obtained in the following Examples and Comparative Examples are evaluated according to the methods described below.

(1) BET Specific Surface Area

The specific surface area of each specimen of the adsorbent was measured by using "BELSORP-mini" available from BEL Japan, Inc.

(2) Volume Mean Particle Diameter

The volume mean particle diameter ($D_{50}$) of each specimen of the adsorbent was measured by using a "Microtrac" particle size distribution measuring device: MT3200 II available from NIKKISO CO., LTD.

(3) Adsorption Test of Indole

An indole solution was prepared by dissolving 30 mg of indole in 300 mL of phosphate buffered saline of pH 7.4. Then, 0.02 g of each specimen of the adsorbent was accommodated in a conical flask equipped with a plug and having a capacity of 100 mL, and 50 mL of the prepared indole solution was added to the flask. The flask was placed in a dark place and its content was shaken at a temperature of 37° C. and a shaking rate of 120 rpm and with an oscillation amplitude of about 3 cm. After the shaking was finished, the content of the flask was filtered with a 0.45 m membrane filter. During the filtration, a first filtrate of about 15 mL was discarded and a subsequent filtrate of about 15 mL was taken as a sample solution.

Then, both of the two solutions, namely, the obtained sample solution and the previously prepared indole solution, were 4-times diluted by water and measured of their total carbon concentration and inorganic carbon concentration by using a total organic carbon analyzer. The organic carbon concentration of each of the two kinds of solutions was calculated by subtracting the measured value of the inorganic carbon concentration from the measured value of the total carbon concentration and by multiplying the obtained difference by four.

Then, the amounts of indole contained in the indole solution and the sample solution were calculated from the obtained value of the organic carbon concentration of each of the two kinds of solutions according to the following formula (1). Further, the ability of adsorption of indole (%) was calculated according to the following formula (2).

$$\text{Amount of indole (mg)} = \text{concentration of organic carbon (mg/L)} \times 50 \text{ (mL)}/1000 \text{ (mL)} \times 117/(12 \times 8) \quad (1)$$

$$\text{Ability of adsorption of indole (\%)} = [(\text{amount of indole in the indole solution} - \text{amount of indole in the sample solution})/(\text{amount of indole in the indole solution})] \times 100 \quad (2)$$

(4) Adsorption Test of Indoleacetic Acid

A 3-indoleacetic acid solution was prepared by dissolving 30 mg of 3-indoleacetic acid in 300 mL of phosphate buffered saline of pH 7.4. Then, 0.05 g of each specimen of the adsorbent was accommodated into a conical flask equipped with a plug and having a capacity of 100 mL, and 50 mL of the prepared 3-indoleacetic acid solution was added to the flask. The flask was placed in a dark place and its content was shaken at a temperature of 37° C. and a shaking rate of 120 rpm and with an oscillation amplitude of about 3 cm. After the shaking was finished, the content of the flask was filtered with a 0.45 μm membrane filter. During the filtration, a first filtrate of about 15 mL was discarded and a subsequent filtrate of about 15 mL was taken as a sample solution.

Then, both of the two solutions, namely, the obtained sample solution and the previously prepared 3-indoleacetic acid solution, were 2-times diluted by water and measured of their total carbon concentration and inorganic carbon concentration by using the total organic carbon analyzer. The organic carbon concentration of each of the two kinds of solutions was calculated by subtracting the measured value of the inorganic carbon concentration from the measured value of the total carbon concentration and by multiplying the obtained difference by two.

Then, the amounts of 3-indoleacetic acid contained in the 3-indoleacetic acid solution and the sample solution were calculated from the obtained value of the organic carbon concentration of each of the two kinds of solutions according to the following formula (3). Further, the ability of adsorption of 3-indoleacetic acid (%) was calculated according to the following formula (4).

$$\text{Amount of 3-indoleacetic acid (mg)} = \text{concentration of organic carbon (mg/L)} \times 50 \text{ (mL)}/1000 \text{ (mL)} \times 175/(12 \times 10) \quad (3)$$

$$\text{Ability of adsorption of 3-indoleacetic acid (\%)} = [(\text{amount of 3-indoleacetic acid in the 3-indoleacetic acid solution} - \text{amount of 3-indoleacetic acid in the sample solution})/(\text{amount of 3-indoleacetic acid in the 3-indoleacetic acid solution})] \times 100 \quad (4)$$

(5) Adsorption Test of Iindoxylsulfuric Acid

A potassium indoxylsulfate solution was prepared by dissolving 30 mg of potassium indoxylsulfate in 300 mL of phosphate buffered saline of pH 7.4. Then, 0.02 g of each specimen of the adsorbent was accommodated into a conical flask equipped with a plug and having a capacity of 100 mL, and 50 mL of the prepared potassium indoxylsulfate solution was added to the flask. The flask was placed in a dark place and its content was shaken at a temperature of 37° C. and a shaking rate of 120 rpm and with an oscillation amplitude of about 3 cm. After the shaking was finished, the content of the flask was filtered with a 0.45 μm membrane filter. During the filtration, a first filtrate of about 15 mL was discarded and a subsequent filtrate of about 15 mL was taken as a sample solution.

Then, both of the two solutions, namely, the obtained sample solution and the previously prepared potassium indoxylsulfate solution, were 2-times diluted by water and measured of their total carbon concentration and inorganic carbon concentration by using the total organic carbon analyzer. The organic carbon concentration of each of the two kinds of solutions was calculated by subtracting the measured value of the inorganic carbon concentration from the measured value of the total carbon concentration and by multiplying the obtained difference by two.

Then, the amounts of potassium indoxylsulfate contained in the potassium indoxylsulfate solution and the sample solution were calculated from the obtained value of the organic carbon concentration of each of the two kinds of solutions according to the following formula (5). Further, the ability of adsorption of potassium indoxylsulfate (%) was calculated according to the following the formula (6).

$$\text{Amount of potassium indoxylsulfate (mg)} = \text{concentration of organic carbon (mg/L)} \times 50 \text{ (mL)}/1000 \text{ (mL)} \times 251/(12 \times 8) \quad (5)$$

$$\text{Ability of adsorption of potassium indoxylsulfate (\%)} = [(\text{amount of potassium indoxylsulfate in the potassium indoxylsulfate solution} - \text{amount of potassium indoxylsulfate in the sample solution})/(\text{amount of potassium indoxylsulfate in the potassium indoxylsulfate solution})] \times 100 \quad (6)$$

Example 1

1000 parts of furfuryl alcohol, 1000 parts of water, 1.5 parts of gum arabic and 15 parts of 10% dodecylbenzene sulfonic acid solution were charged into a reaction vessel provided with a thermometer, a stirring device and a reflux condenser. The content of the reaction vessel was heated to a temperature of 80° C. while being stirred and mixed to cause a reaction (self-condensation reaction) for two hours. Then, the content was further subjected to a reaction (curing reaction) at a temperature of 100° C. for four hours. After the reaction was finished, the inside of the reaction vessel was cooled to the room temperature, and the liquid reaction product was filtered and purified so as to obtain cured spherical particles of the furfuryl alcohol resin.

Then, 300 parts of the obtained cured spherical particles of the furfuryl alcohol resin were carbonized by heating (firing) at a temperature of 800° C. for 30 minutes in a nitrogen atmosphere by using a rotary kiln so as to obtain spherical particles of carbon. The obtained spherical particles of carbon were successively activated with a steam in a nitrogen atmosphere at a temperature of 900° C. for four hours so as to obtain spherical particles of activated carbon. The obtained particles of activated carbon were oxidized in an air atmosphere at a temperature of 475° C. for three hours and 15 minutes, and then deoxidized or reduced at a temperature of 800° C. for 5 minutes so as to obtain an orally administered adsorbent.

The properties (BET specific surface area; average particle diameter; ability of adsorption of indole, indoleacetic acid, and indoxylsulfuric acid) of the thus obtained orally administered adsorbent were evaluated and shown in the following Table 1.

Example 2

1000 parts of furfuryl alcohol, 1000 parts of water, 1.5 parts of gum arabic and 15 parts of 10% dodecylbenzene sulfonic acid solution were charged into a reaction vessel provided with a thermometer, a stirring device and a reflux condenser. The content of the reaction vessel was heated to a temperature of 80° C. while being stirred and mixed to conduct a reaction (self-condensation reaction) for two hours. Then, the content was further subjected to a reaction (curing reaction) at a temperature of 100° C. for four hours. After the reaction was finished, the inside of the reaction vessel was cooled to the room temperature, and the liquid reaction product was filtered and purified so as to obtain cured spherical particles of the furfuryl alcohol resin.

Then, 300 parts of the obtained cured spherical particles of the furfuryl alcohol resin were carbonized by heating (firing) at a temperature of 800° C. for 30 minutes in a nitrogen atmosphere by using a rotary kiln so as to obtain spherical particles of carbon. The obtained spherical particles of carbon were successively activated with a steam in a nitrogen atmosphere at a temperature of 800° C. for 14 hours so as to obtain spherical particles of activated carbon. The obtained particles of activated carbon were oxidized in an air atmosphere at a temperature of 475° C. for three hours and 15 minutes, and then deoxidized at a temperature of 800° C. for 5 minutes so as to obtain an orally administered adsorbent.

The properties (BET specific surface area; average particle diameter; ability of adsorption of indole, indoleacetic acid, and indoxylsulfuric acid) of the thus obtained orally administered adsorbent were evaluated and shown in the following Table 1.

Example 3

1000 parts of furfuryl alcohol, 1000 parts of water, 1.5 parts of hydroxyethyl cellulose and 15 parts of 10% dodecylbenzene sulfonic acid solution were charged into a reaction vessel provided with a thermometer, a stirring device and a reflux condenser. The content of the reaction vessel was heated to a temperature of 80° C. while being stirred and mixed to conduct a reaction (self-condensation reaction) for two hours. Then, the content was further subjected to a reaction (curing reaction) at a temperature of 100° C. for four hours. After the reaction was finished, the inside of the reaction vessel was cooled to the room temperature, and the liquid reaction product was filtered and purified so as to obtain cured spherical particles of the furfuryl alcohol resin.

Then, 300 parts of the obtained cured spherical particles of the furfuryl alcohol resin were carbonized by heating (firing) at a temperature of 800° C. for 30 minutes in a nitrogen atmosphere by using a rotary kiln so as to obtain spherical particles of carbon. The obtained spherical particles of carbon were successively activated with a steam in a nitrogen atmosphere at a temperature of 900° C. for four hours so as to obtain spherical particles of activated carbon. The obtained particles of activated carbon were oxidized in an air atmosphere at a temperature of 475° C. for three hours and 15 minutes, and then deoxidized at a temperature of 800° C. for 5 minutes so as to obtain an orally administered adsorbent.

The properties (BET specific surface area; average particle diameter; ability of adsorption of indole, indoleacetic acid, and indoxylsulfuric acid) of the thus obtained orally administered adsorbent were evaluated and shown in the following Table 1.

Comparative Example 1

1000 parts of furfuryl alcohol, 1240 parts of 37% formalin, 700 parts of water, 10 parts of hydroxyethyl cellulose and 25 parts of 10% dodecylbenzene sulfonic acid solution were charged into a reaction vessel provided with a thermometer, a stirring device and a reflux condenser. The content of the reaction vessel was heated to a temperature of 80° C. while being stirred and mixed to conduct a reaction for two hours. Then, the content was further subjected to a reaction at a temperature of 100° C. for four hours. After the reaction was finished, the inside of the reaction vessel was cooled to the room temperature, and the liquid reaction product was filtered and purified so as to obtain cured spherical particles of a furan resin.

Then, 300 parts of the obtained cured spherical particles of the furan resin were carbonized by heating (firing) at a temperature of 800° C. for 30 minutes in a nitrogen atmosphere by using a rotary kiln so as to obtain spherical particles of carbon. The obtained spherical particles of carbon were successively activated with a steam in a nitrogen atmosphere at a temperature of 900° C. for four hours so as to obtain spherical particles of activated carbon. The obtained particles of activated carbon were oxidized in an air atmosphere at a temperature of 475° C. for three hours and 15 minutes, and then deoxidized at a temperature of 800° C. for 5 minutes so as to obtain an orally administered adsorbent.

The properties (BET specific surface area; average particle diameter; ability of adsorption of indole, indoleacetic acid, and indoxylsulfuric acid) of the thus obtained orally administered adsorbent were evaluated and shown in the following Table 1.

Comparative Example 2

1000 parts of phenol, 1035 parts of 37% formalin, 758 parts of water, 10.5 parts of hydroxyethyl cellulose and 100 parts of 10% dodecylbenzene sulfonic acid solution were charged into a reaction vessel provided with a thermometer, a stirring device and a reflux condenser. The content of the reaction vessel was heated to a temperature of 80° C. while being stirred and mixed to conduct a reaction for 6 hours. After the reaction was finished, the inside of the reaction vessel was cooled to the room temperature, and the liquid reaction product was filtered and purified so as to obtain cured spherical particles of a phenolic resin.

Then, 300 parts of the obtained cured spherical particles of the phenolic resin were carbonized by heating (firing) at a temperature of 800° C. for 30 minutes in a nitrogen atmosphere by using a rotary kiln so as to obtain spherical particles of carbon. The obtained spherical particles of carbon were successively activated with a steam in a nitrogen atmosphere at a temperature of 900° C. for four hours so as to obtain spherical particles of activated carbon. The obtained particles of activated carbon were oxidized in an air atmosphere at a temperature of 475° C. for three hours and 15 minutes, and then deoxidized at a temperature of 800° C. for 5 minutes so as to obtain an orally administered adsorbent.

The properties (BET specific surface area; average particle diameter; ability of adsorption of indole, indoleacetic acid, and indoxylsulfuric acid) of the thus obtained orally administered adsorbent were evaluated and shown in the following Table 1.

Comparative Example 3

The properties of a commercially available spherical carbon adsorbent: Merckmezin (available from Mylan Inc.) produced by using a phenolic resin as its starting material were evaluated similarly as described above and the results were shown in the following Table 1.

Among the adsorbents of Comparative Examples 1-3, even the adsorbent of Comparative Example 1 obtained by using the spherical particles of the furan resin, which is similar to the resin material used in the present invention, is inferior to the adsorbents according to the present invention in the ability of adsorption of indoxylsulfuric acid.

The invention claimed is:

1. A method of producing an orally administered adsorbent, comprising the steps of:
   preparing spherical particles of a furfuryl alcohol resin through a self-condensation reaction of furfuryl alcohol in the presence of an acid catalyst and a protective colloid and curing of the self-condensation reaction product;
   obtaining spherical particles of carbon by carbonizing the spherical particles of the furfuryl alcohol resin at a temperature of 400-900° C.; and
   forming spherical particles of activated carbon by activating the obtained spherical particles of carbon at a temperature of 700-1000° C.,
   wherein the adsorbent has an average particle diameter of 150-1000 μm and a specific surface area of 1000-1800 $m^2/g$ measured by the BET method.

2. The method according to claim 1, wherein the protective colloid is a water-soluble high-molecular compound.

3. The method according to claim 2, wherein the water-soluble high-molecular compound is gum arabic.

4. The method according to claim 1, wherein the acid catalyst has a pKa of less than 1.5.

5. The method according to claim 4, wherein the acid catalyst is alkylbenzene sulfonic acid.

6. The method according to claim 1, wherein the reaction of the furfuryl alcohol is conducted in the presence of water as a reaction medium.

TABLE 1

| | EXAMPLE 1 | EXAMPLE 2 | EXAMPLE 3 | COMPARATIVE EXAMPLE 1 | COMPARATIVE EXAMPLE 2 | COMPARATIVE EXAMPLE 3 |
|---|---|---|---|---|---|---|
| MATERIAL MONOMER/RESIN | furfuryl alcohol | furfuryl alcohol | furfuryl alcohol | furfuryl alcohol/formalin | phenolic resin | phenolic resin |
| BET SPECIFIC SURFACE AREA [$m^2/g$] | 1551 | 1389 | 1440 | 1380 | 1452 | 1383 |
| AVERAGE PARTICLE DIAMETER [μm] | 355 | 346 | 381 | 301 | 387 | 299 |
| ABILITY OF ADSORPTION OF INDOXYLSULFURIC ACID [%] | 69 | 67 | 70 | 54 | 42 | 10 |
| ABILITY OF ADSORPTION OF INDOLEACETIC ACID [%] | 84 | 77 | 84 | 75 | 56 | 41 |
| ABILITY OF ADSORPTION OF INDOLE [%] | 85 | 85 | 87 | 80 | 77 | 52 |

As is apparent from the results shown in Table 1, the adsorbents comprising the spherical particles of activated carbon obtained in Examples 1-3 according to the present invention exhibited a significantly high ability of adsorption of each of indoxylsulfuric acid, indoleacetic acid and indole.

On the other hand, the adsorbents comprising the spherical particles of activated carbon obtained in Comparative Examples 1-3 failed to have a sufficient ability of adsorption of each of indoxylsulfuric acid, indoleacetic acid and indole.

7. The method according to claim 1, wherein the reaction of the furfuryl alcohol is conducted at a temperature of not lower than 50° C.

8. The method according to claim 1, wherein the obtained spherical particles of activated carbon are subjected to oxidizing and/or reducing treatment(s) so as to modify a surface condition of the spherical particles of the activated carbon.

* * * * *